United States Patent [19]

Sinofsky

[11] Patent Number: 5,569,239
[45] Date of Patent: *Oct. 29, 1996

[54] PHOTOREACTIVE SUTURING OF BIOLOGICAL MATERIALS

[75] Inventor: Edward L. Sinofsky, Dennis, Mass.

[73] Assignee: Rare Earth Medical, Inc., West Yarmouth, Mass.

[21] Appl. No.: 292,608

[22] Filed: Aug. 18, 1994

[*] Notice: The term of this patent shall not extend beyond the expiration date of Pat. No. 5,207,670.

Related U.S. Application Data

[63] Continuation of Ser. No. 56,192, May 3, 1993, abandoned, which is a continuation of Ser. No. 804,791, Dec. 9, 1991, Pat. No. 5,207,670, which is a continuation-in-part of Ser. No. 538,977, Jun. 15, 1990, Pat. No. 5,071,417.

[51] Int. Cl.⁶ .................................................. A61N 5/06
[52] U.S. Cl. .......................... 606/8; 606/10; 606/12; 606/213; 128/898
[58] Field of Search ................ 606/2, 3, 7, 8, 606/9, 1, 13, 213–216, 219; 607/88, 89; 128/898

[56] References Cited

U.S. PATENT DOCUMENTS

| | | | |
|---|---|---|---|
| 3,272,204 | 9/1966 | Artandi et al. | 606/229 X |
| 3,276,448 | 10/1966 | Kronenthal | 606/229 X |
| 3,376,869 | 4/1968 | Borysko | 606/229 X |
| 3,593,985 | 7/1971 | Tanner, Jr. | 606/213 X |
| 3,808,113 | 4/1974 | Okamura et al. | 606/229 X |
| 3,988,782 | 11/1976 | Dardik et al. | 606/229 X |
| 4,034,750 | 7/1977 | Seiderman | 606/229 X |
| 4,316,467 | 2/1982 | Muckerheide | 606/9 |
| 4,428,376 | 1/1984 | Mericle | 606/219 |
| 4,485,816 | 12/1984 | Krumme | 606/219 |
| 4,523,591 | 6/1985 | Kaplaw et al. | 606/219 |
| 4,969,912 | 11/1990 | Kelman et al. | 604/51 X |
| 5,066,299 | 11/1991 | Bellingham | 606/213 |
| 5,100,429 | 3/1992 | Sinofsky et al. | 128/DIG. 8 |
| 5,156,613 | 10/1992 | Sawyer | 606/214 X |
| 5,207,670 | 5/1993 | Sinofsky | 606/8 |
| 5,209,776 | 5/1993 | Bass et al. | |

FOREIGN PATENT DOCUMENTS

WO92/12673  8/1992  WIPO .

*Primary Examiner*—Angela D. Sykes
*Assistant Examiner*—Michael Peffley
*Attorney, Agent, or Firm*—Thomas J. Engellenner; Lahive & Cockfield

[57] ABSTRACT

Materials and methods for photoreactive suturing of biological tissue are disclosed. The suture material includes a structure adapted for positioning at an anastomotic site and has at least a portion of the structure formed by a photoreactive crosslinking agent, such that upon irradiation of the structure the crosslinking agent adheres to the biological material. In one embodiment, the suture material can also include a high tensile strength element which is coated with a laser activatable crosslinking agent or glue. The suture methods can be practiced manually, or with various apparatus, such as endoscopes, catheters or hand-held instruments.

21 Claims, 5 Drawing Sheets

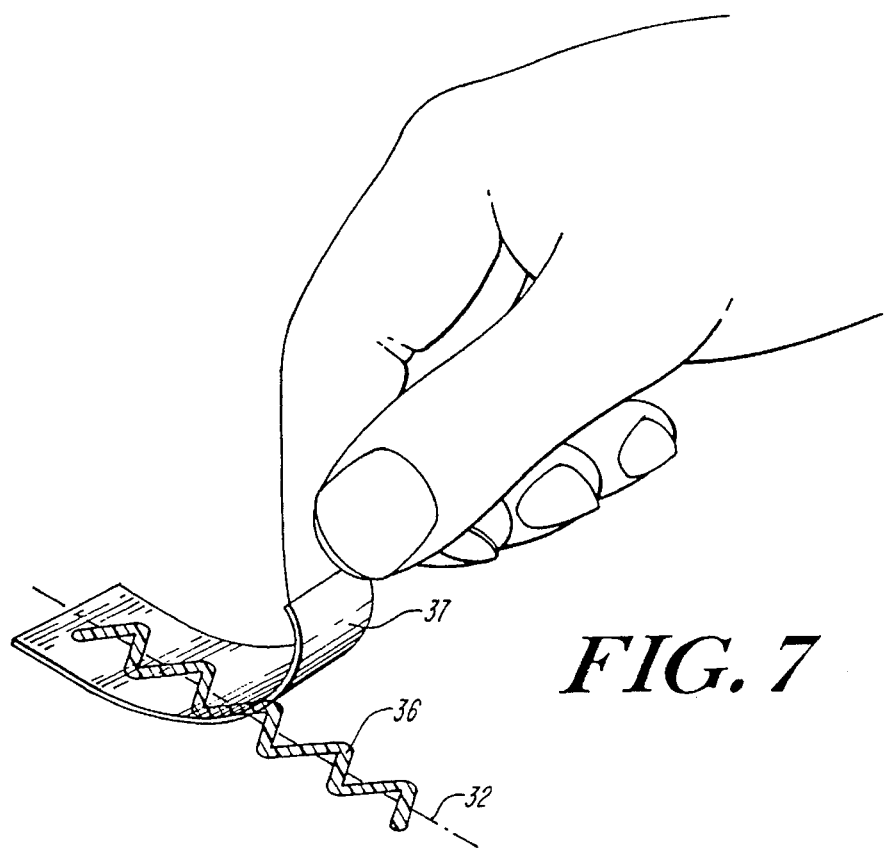
FIG. 7
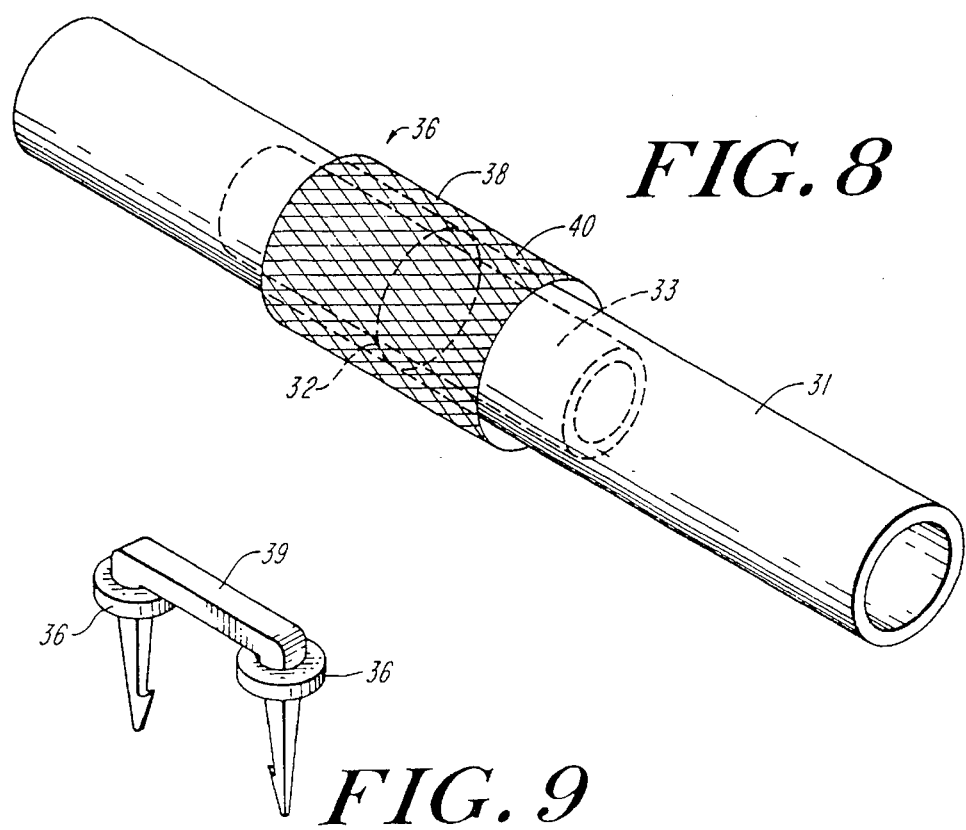
FIG. 8
FIG. 9

PHOTOREACTIVE SUTURING OF BIOLOGICAL MATERIALS

Reference to Related Application

This application is a continuation of application Ser. No. 08/056,192, filed on May 3, 1993, abandoned, which is a continuation of Ser. No. 07/804,791, filed Dec. 9, 1991, now U.S. Pat. No. 5,207,670, which is a continuation-in-part of Ser. No. 538,977, filed Jun. 15, 1990 now U.S. Pat. No. 5,071,417.

BACKGROUND OF THE INVENTION

The technical field of this invention is surgery and, in particular, method and materials for joining living tissues and promoting the healing of small biological structures.

The conventional approach to joining tissue segments following surgery, injury or the like, has been to employ mechanical sutures or staples. While these techniques are often successful, there are a number of limitations inherent in such mechanical approaches. First, the practice of suturing or stapling tissue segments together is limited by the eyesight and the dexterity of the surgeon which can present a severe constraint when anastomosing tiny biological structures. Second, when delicate biological tissues or organs are sutured, even minimal scarring can affect the function of the structure. Finally, suturing can be less than satisfactory, even when properly performed, because of the gaps which are left between the stitches, the inherent weakness of the joint, or the possibility of progressive structural weakening over time.

Various researchers have proposed the use of laser energy to fuse biological tissues together. For example, Yahr et al. in an article in *Surgical Forum*, pp. 224–226 (1964), described an attempt at laser anastomosis of small arterial segments with a neodymium laser. However, the neodymium laser used by Yahr et al. operated at a wavelength of about 1.06 micrometers was not efficiently absorbed by the tissue, requiring large amounts of energy to effect fusion, while also affecting too large of a tissue volume.

Further research on laser fusion involving various alternative laser sources, such as the carbon dioxide laser emitting laser light at about 10.6 micrometers, the argon laser emitting light at about 0.50 micrometers, and the ruby laser emitting light at about 0.70 micrometers, continued to encounter problems. In particular, the output of carbon dioxide lasers was found to be heavily absorbed by water and typically penetrated into water-laden tissue only to a depth to about 20 micrometers. This penetration depth and the resulting bond induced by carbon dioxide laser fusion was too shallow to provide durable bonding in a physiological environment.

Argon and other visible light laser also produced less than satisfactory effects. The output of argon lasers and the like was found to be heavily absorbed by blood and subject to substantial scattering within the tissue. These effects combined to create a narrow therapeutic "window" between a proper amount of energy necessary for laser fusion and that which induces tissue carbonization, particularly in pigmented tissues and tissues that have a high degree of vascularization. Moreover, argon lasers have been particularly cumbersome devices, requiring large amounts of electricity and cooling water.

Recently, the development of new solid state laser sources have made prospects brighter for efficient, compact laser fusion systems suitable for clinical use. Such systems typically employ rare earth-doped yttrium aluminum garnet (YAG) or yttrium lithium fluoride (YLF) or yttrium-scadium-golilinium-garnet (YSGG) lasers. See, for example, U.S. Pat. Nos. 4,672,969 and 4,854,320 issued to Dew, disclosing the use of a neodymium-doped YAG laser to induce laser fusion of biological materials and to obtain deeper tissue penetration. However, even with such solid state laser sources, the problems of scattering and damage to adjacent tissue remain. The Dew patents disclose the use of computer look-up tables to control the laser dose based on empirical data.

The absorptive properties of biological structures differ considerably from one tissue type to another, as well as from individual to individual, making dosage look-up tables often unreliable. There exists a need for better methods and materials for accurately controlling the formation of anastomotic bonds which avoid thermal damage and achieve optimal results. In particular, non-mechanical suture materials which can take advantage of laser or other high energy light sources to join biological materials together or otherwise make repairs to delicate body tissues would satisfy a long-felt need in the art.

SUMMARY OF THE INVENTION

Materials and methods for photoreactive suturing of biological tissue are disclosed. The suture material includes a structure adapted for positioning at an anastomotic site and has at least a portion of the structure formed by a photoreactive crosslinking agent, such that upon irradiation of the structure the crosslinking agent adheres to the biological material. In one embodiment, the suture material can also include a high tensile strength element which is coated with a laser activatable crosslinking agent or glue. The suture methods can be practiced manually, or with various apparatus, such as endoscopes, catheters or hand-held instruments.

The present invention can employ various "biological glue" materials as crosslinking agents in either solid, liquid, gel or powder form to form a bond to tissue segments and thereby hold them together while natural healing processes occur. The crosslinking agents should be biocompatible and are preferably biodegradable over time in vivo. Examples of such crosslinking agents include collagen, elastin, fibrin, albumin and various other photoreactive polymeric materials.

Various strength enhancing agents can also be incorporated into the suture structure to provide additional tensile support along and across the anastomosis. Such high tensile strength elements can be formed from pre-crosslinked segments of the same material that forms the photoreactive crosslinking agent, or they can be formed from strips or fibers of other natural or synthetic biodegradable materials such as cotton or polyesters, to enhance the strength of the bond.

The present invention permits the creation of anastomoses of biological structures with the optimal use of appropriate laser energy, minimizing the total energy delivered to the site while obtaining maximum bond strength and integrity. The terms "anastomosis" and "anastomotic site" are used herein to broadly encompass the joinder of biological structures, including, for example, incision and wound healing, repair of blood vessels and other tubular structures, sealing of fissures, nerve repairs, reconstructive procedures, and the like.

The present invention is preferably practiced in conjunction with a high energy light source, such as laser, for delivery of a beam of radiation to an anastomotic site, and can also employ a reflectance sensor for measuring light reflected from the site and a controller for monitoring changes in the reflectance of the light from the site and controlling the laser in response to the reflectance changes.

In one embodiment, the laser radiation is delivered through a hand-held instrument via an optical fiber. The instrument can also include one or more additional fibers for the delivery of illumination light or radiation from a laser diode (which can be broadband or white light or radiation from a laser diode) which is reflected and monitored by the reflectance sensor. Reflectance changes during the course of the suturing operation at one or more wavelengths can be monitored (or compared) to provide an indication of the degree of tissue crosslinking and determine when an optimal state of fusion has occurred.

In the present invention, reflective feedback is used to monitor the state of crosslinking of the suture material with the biological material, as well as the degree of fusion or coagulation of the biological structures so as to allow an optimal dose by either manipulation of the energy level or exposure time, or by controlling the sweep of energy across an exposure path. Reflectance changes can also be employed by a control means in the present invention to adjust or terminate laser operation.

Various light sources can be employed, including gas, liquid and solid state laser media. Because the present invention permits the user to carefully monitor the energy dosage, solid state lasers can be utilized instead of the more conventional (and cumbersome) gas lasers. Such solid state laser include optically-pumped (e.g., lamp or diode pumped) laser crystals, diode lasers, and diode pumped optical fibers. Tunable laser sources can also be used to practical advantage in the present invention. In some applications, high intensity flash lamps can also be employed in lieu of a laser source. Since the feedback control systems disclosed herein eliminate (or reduce) the need for look-up tables, a tunable laser source can be used to full advantage by matching the laser output wavelength with the absorptive and/or dimensional characteristics of the biological structures to be repaired or otherwise joined. In one embodiment of the invention, the laser source can be tuned over at least a portion of a wavelength range from about 1.4 micrometers to about 2.5 micrometers to match particular tissue profiles.

In another aspect of the invention, a real-time display means is disclosed which can be incorporated into a surgical microscope or goggles worn by the clinician during the procedure to provide a visual display of the state of tissue coagulation simultaneously with the viewing of the surgical site. The display can reveal reflectance values at one or more specific wavelengths (preferably, chosen for their sensitivity to the onset and optimal state of tissue crosslinking), as well as display a warning of the onset of tissue carbonization.

In one method, according to the invention, a technique for photoreactive suturing of biological structures is disclosed in which laser energy is applied to join together two or more tissue segments via a suture structure that includes a photoreactive crosslinking agent, while the reflectance of light from the irradiated site is monitored. Changes in scattering due to crosslinking of the tissue and crosslinking agent will cause reflectance changes. The reflectance can be monitored in real-time to determine the optimal exposure duration or aid as visual feedback in the timing used in sweeping the energy across the anastomosis during the suturing procedure.

The method can further be enhanced by employing a suturing material which incorporates high tensile strength elements, and/or by coating the entire anastomotic site with a biological glue. The reinforcing strips provide load support across and along the repair line, and preferably are also bonded by the crosslinking agent to the tissue, itself, providing superior bond strength.

The depth of penetration of the laser energy can be controlled in one embodiment by tuning a mid-infrared laser along a range of wavelengths from about 1.4 micrometers to about 2.5 micrometers to adjust the penetration to match the desired weld depth. Tuning can be accomplished, for example, by mechanical or electro-optical variation in the orientation of a birefringent crystal disposed in the laser beam path.

This allows the clinician to select a weld depth appropriate to the size and type of structures to be welded. This feature of the invention can be particularly advantageous with delicate biological structures where accuracy is needed to crosslink only what is necessary for temporary strength, while avoiding thermal denaturing of critical structures that cannot function once scarred. In most instances, the patient's body will metabolize the suture material over time simultaneous with (or following) the natural healing of the repair site by physiological processes.

The invention will next be described in connection with certain illustrated embodiments; however, it should be clear by those skilled in the art that various modifications, additions and subtractions can be made without departing from the spirit or scope of the invention.

BRIEF DESCRIPTION OF THE DRAWINGS

FIG. 7 is a schematic illustration of a suture material and detachable carrier according to the invention;

FIG. 8. is a schematic illustration of a tubular suture material according to the invention;

FIG. 9 is a schematic illustration of a staple-like suture material according to the invention;

DETAILED DESCRIPTION

Figure 1:
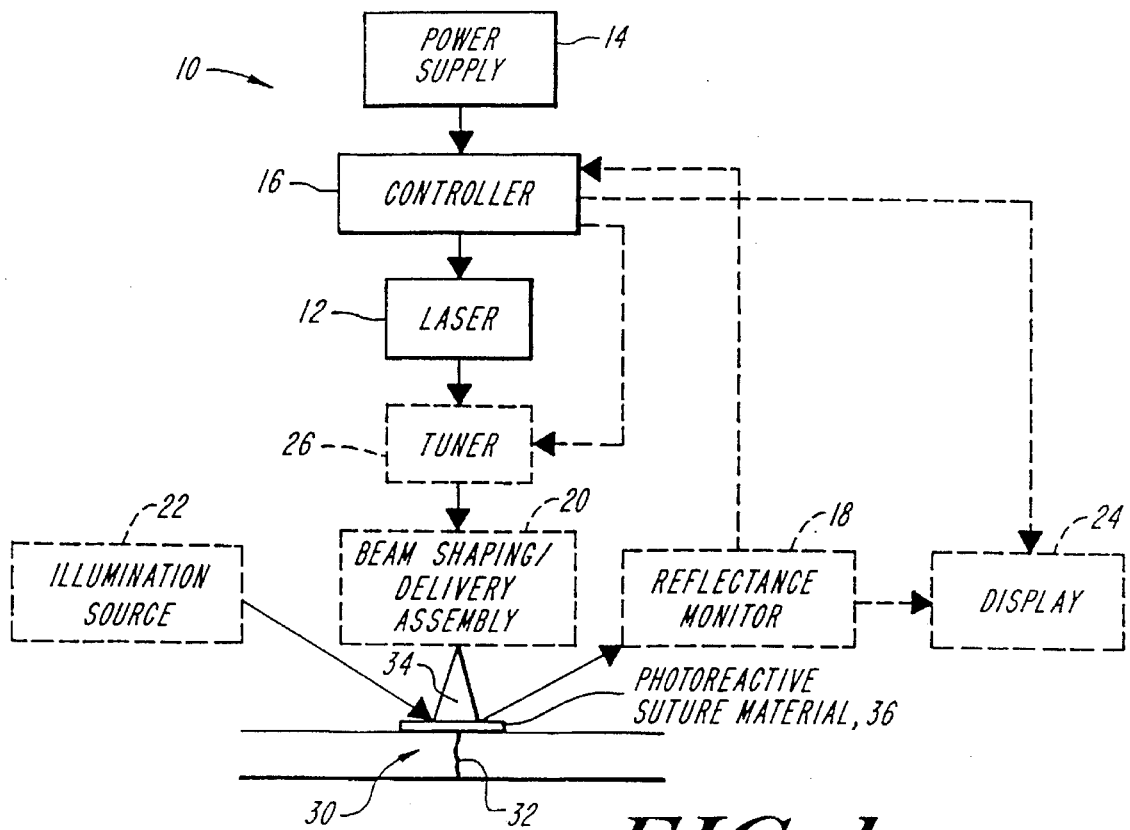
FIG. 1 is a schematic block diagram of a photoreactive suturing system according to the present invention.

In FIG. 1, a schematic block diagram of a photoreactive suturing system 10 is shown, including a laser 12, power supply 14, controller 16 and photoreactive suturing material 36. The system can further include a beamshaping/delivery assembly 20, illumination source 22, reflectance monitor 18, display 24 and tuner 26. In use, the output of laser 12 is delivered, preferably via beamshaping/delivery assembly 20, to an anastomotic site 30 to fuse the suture material 36 on opposite sides of a fissure or cleavage line 32 in a biological material. As the laser beam irradiates exposure zone 34, a crosslinking reaction occurs to fuse the suture material and the biological tissue in the vicinity of the site 30. The degree of crosslinking can be determined by the reflectance monitor 18, which provides electrical signals to controller 16 in order to control the procedure. The reflectance monitor 18 preferably receives light reflected by the site from a broadband or white light illumination source 22. In addition to controlling the laser operation automatically, the reflectance monitor 18 and/or controller 16 can also provide signals to a display 24 to provide visual (and/or audio) feedback to the clinical user, thereby permitting manual control. Tuner 26 can also be employed by the user (or automatically controlled by controller 16) to adjust the wavelength of the annealing radiation beam.

Figure 2:
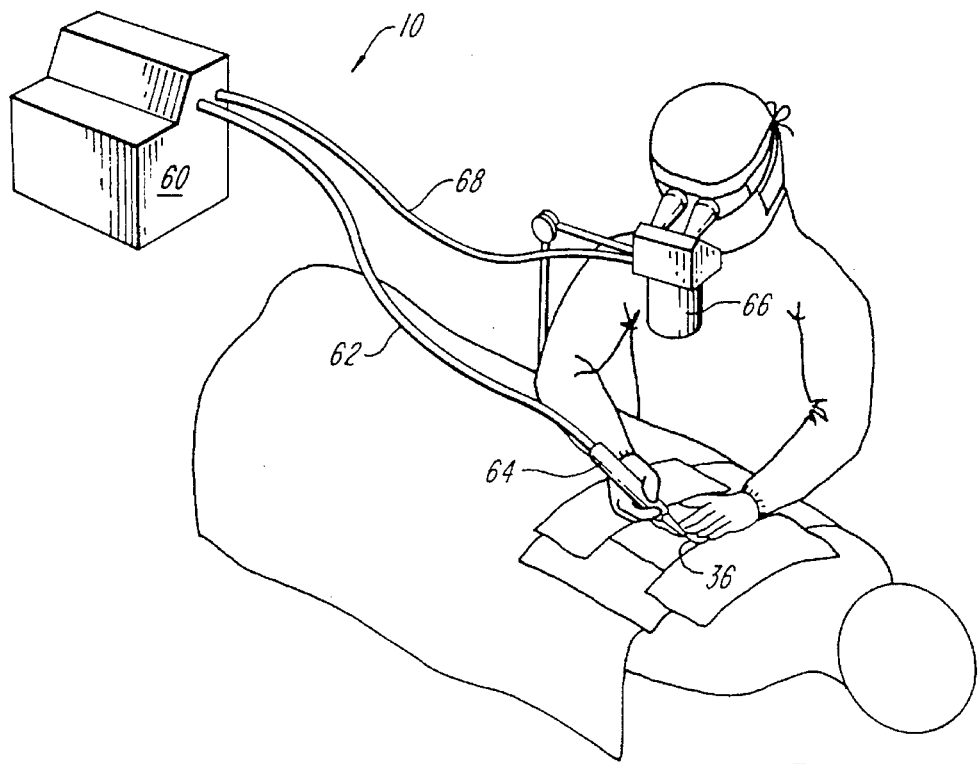
FIG. 2 is a perspective view of a clinical system embodying the principles of the invention.

FIG. 2 provides further schematic illustration of the photoreactive suture system 10 in use. The electrical and optical components of the system can be housed in a system cabinet 60 suitable for use in an operating room or other clinical environment. The laser output is delivered to the patient by an optical fiber cable 62 (which can include multiple optical fibers as detailed below) and a handpiece 64. The system is preferably used in conjunction with a surgical microscope (or goggles) 66 which are adapted to provide a "heads-up" display to the user. Display signals from the system cabinet 60 are transmitted to the microscope (or goggles) 66 by cable 68. The laser output can also be delivered to a remote site via an arthroscope, endoscope or catheter and the display features of such an instrument can be similarly adapted to provide the user with data on progress of the crosslinking reaction.

The suture materials of the present invention can take various forms. In the simplest embodiment, the suture material comprises a strip or strand of a photoreactive crosslinking agent, such a collagen fibers, which can be sewn or draped upon a fissure or incision and then crosslinked to the tissue to provide closure. Once in place, the suture material is irradiated with laser or other high intensity light energy to fuse the suture to the anastomotic site.

Figure 3:
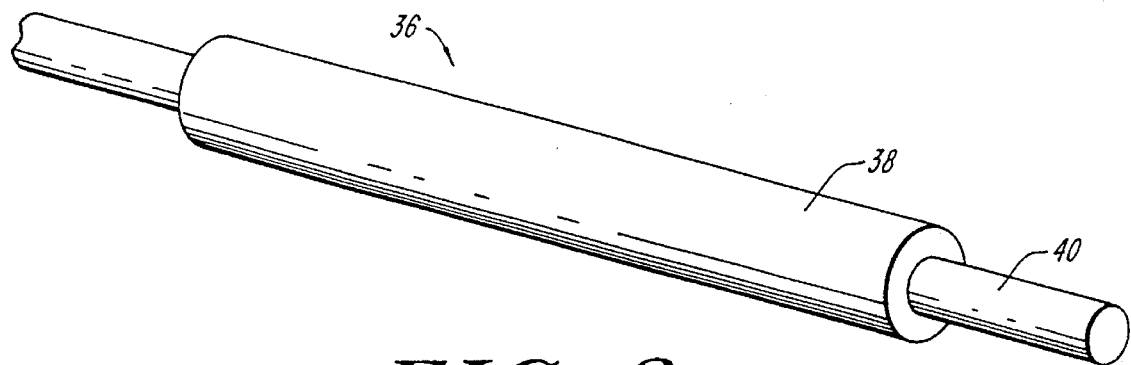
FIG. 3 is a schematic illustration of a suture material incorporating a high tensile strength element according to the invention.

Alternatively, as shown in FIG. 3, the suture material 36 can include a high tensile strength core element 40 and an outer cross-linkable agent 38 which are likewise used to sew or drape the anastomotic site prior to irradiation and fusion.

Figure 4:
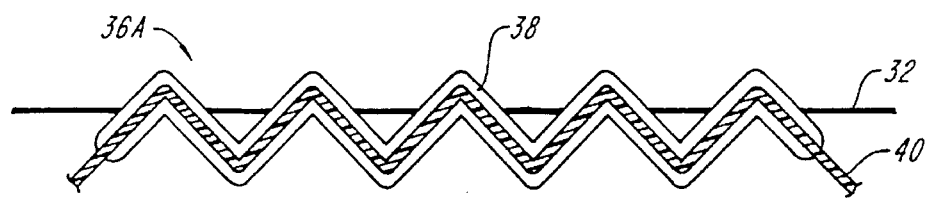
FIG. 4 is a schematic illustration of another suture material according to the invention.

In another embodiment, as shown in FIG. 4, a suture material 36A can be employed which is fabricated in a zig-zag strip form and applied directly upon the incision or fissure 32 to close the opening. Again, suture material 36A can include a high tensile strength core element 40 and an outer cross-linkable agent 38.

Figure 5:
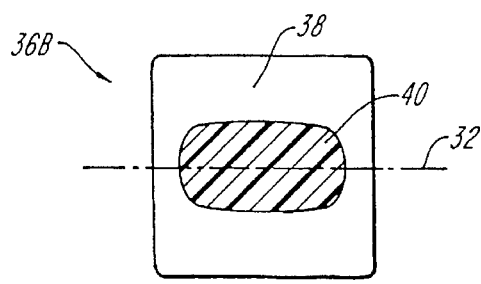
FIG. 5 is a schematic illustration of a yet another suture material according to the invention.
Figure 6:
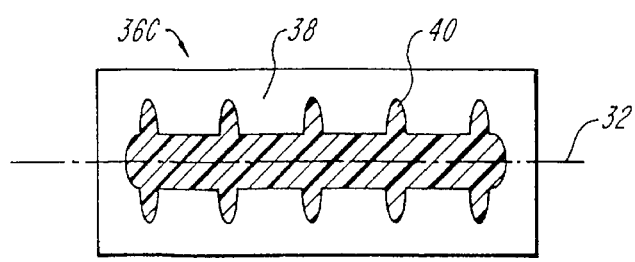
FIG. 6 is a schematic illustration of a further suture material according to the invention.

In further embodiments 36B and 36C, shown in FIGS. 5 and 6, respectively, the suture material can be fabricated as a patch with a high strength element 40 incorporated into the structure, and also including a crosslinking agent 38 to join the suture material to the underlying tissue and thereby effect closure of the anastomotic site 32. In the embodiments of FIGS. 5 and 6, the high strength element 40 can be fabricated, for example, from the same material as the bonding agent 38, but pre-crosslinked to provide the addition resistance to tearing or shearing forces as the wound heals.

The present invention can employ various materials as crosslinking agents in either solid, liquid, gel or powder form to form a bond to tissue segments and thereby hold them together while natural healing processes occur. The crosslinking agents should be biocompatible and are preferably biodegradable over time in vivo. Examples of such crosslinking agents include collagen, elastin, fibrin, albumin and various other photoreactive polymeric materials.

Various strength enhancing agents can also be incorporated into the suture structure to provide additional tensile support along and across the anastomosis. Such high tensile strength elements can be formed from pre-crosslinked segments of the same material that forms the photoreactive crosslinking agent, or they can be formed from strips or fibers of other natural or synthetic biodegradable materials such as polyesters, to enhance the strength of the bond.

In FIG. 7, a detachable carrier 37 is shown for use in applying a zig-zag type strip of crosslinking agent 36 to an anastomotic site 32. In one preferred embodiment, the detachable carrier 37 is substantially transparent to photoirradiation and can be detached from said crosslinking agent 36 following the bonding of the agent to the biological material.

In FIG. 8, a tubular suture material 36 is shown for repairing a torn blood vessel 31 or other body tube or lumen. The suture material 36 preferably includes a crosslinking agent 38 and reinforcing elements which can be braided, woven or simply matted fibers 40. In use, the suture material is either fitted over the severed lumen (in the case of a tube-shaped suture material) or wrapped around the severed biological structure (e.g., with a strip-like suture material), and then irradiated to crosslink the materials together. In some applications, the tubular suture material 36 of FIG. 8 can be designed to shrink as the crosslinking reaction occurs and thereby more tightly wrap the anastomotic site. In such procedures, it may also be preferable to first dispose a stent 33 or similar support within the lumen to prevent collapse.

In FIG. 9, a staple structure 37 is shown incorporating a crosslinking agent 36 on each prong such that the staple can be applied to close a wound and then fused in place by application of laser radiation to the crosslinking agent 36. Alternatively, the entire staple can be formed from a crosslinking agent and then irradiated (e.g., such that the exposed prongs are melted into tissue-bonding balls) to fuse the staple in place. (A similar approach can be taken to "knot," or otherwise secure conventionally sewn sutures when a crosslinking agent comprises, or forms part of, the suture thread; in such an application, the surgeon would put the stitches in place and then irradiate the site in order to bond the suture thread to tissue or itself and thereby increase the strength of the closure.)

The present invention can be practiced with a wide variety of laser sources, including both gas and solid state lasers, operating in either continuous wave ("c.w.") or pulsed modes. More specifically, the laser sources can be carbon monoxide, carbon dioxide, argon lasers or various excimer lasers utilizing mixtures of halogen and noble gases, such as argon-flouride, krypton-fluoride, xenon-chloride and xenon-fluoride. Additionally, the laser can be a solid state laser employing a rare, earth-doped Yttrium Aluminum Garnet (YAG) or Yttrium Lithium Fluoride (YLF) or a Yttrium-Scandium-Gadolinium-Garnet (YSGG) laser.

In one preferred embodiment, the laser source is a rare, earth-doped, solid state laser, such as a holmium-doped, erbium-doped or thulium-doped solid state laser of the YAG, YLF or YSGG type which can be operated in a low wattage c.w. or pulsed mode with an output wavelength in the range of about 1.4 to about 2.5 micrometers and a power density of about 0.1 watt/mm$^2$ to about 1.0 watt/mm$^2$. Such laser sources are disclosed in U.S. Pat. No. 4,917,084 issued on Apr. 17, 1990, to the present inventor and incorporated herein by reference.

The absorption of laser energy from such solid state laser sources by biological tissues is relatively high in relation to the absorption of such energy by water, thereby providing an absorption length in the subject's body of about 100 microns or more. Thus, it is possible to operate satisfactorily even with 10–20 micrometers of blood between the handpiece tip and the anastomotic site.

Figure 10:
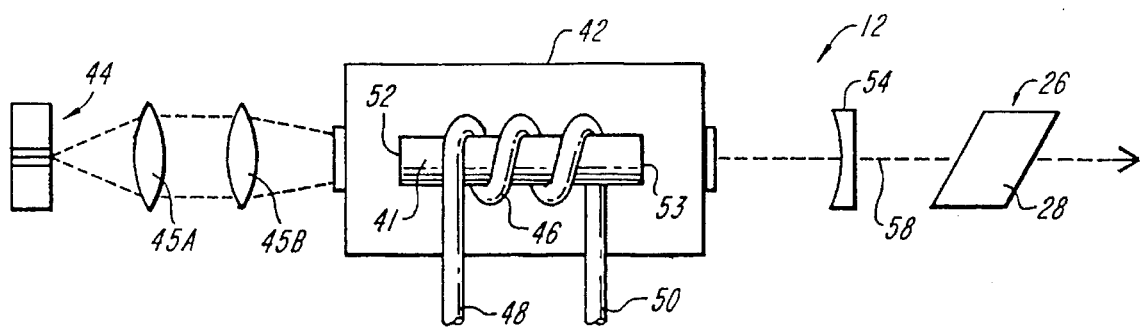
FIG. 10 is a more detailed schematic diagram of a laser source useful in the system of FIG. 1.
Figure 11:
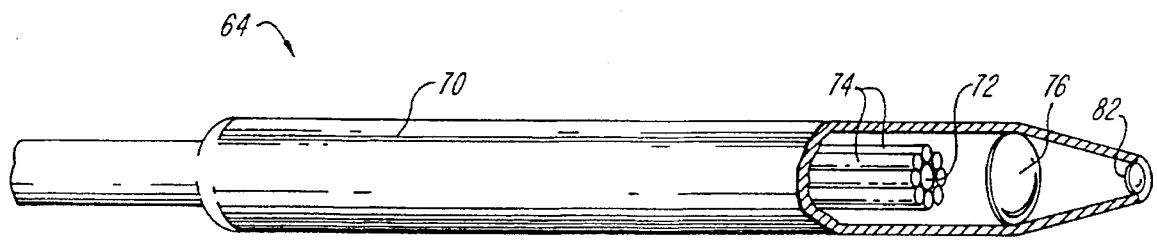
FIG. 11 is a partial, cross-sectional view of a laser beam delivery handpiece according to the invention.

FIG. 10 is a schematic illustration of laser source 12, including a solid-state laser crystal 41, vacuum chamber 42 and diode pump source 44. The laser crystal 41 is preferably surrounded by a cooling quartz or fused-silica jacket 46 having inlet pipe 48 and an outlet pipe 50 for circulation of liquid nitrogen or other cryogenic coolant. The laser cavity can be formed by input crystal face coating 52 and partially-reflective output mirror 54.

Generally, the laser crystal 41 is excited by optical pumping, that being, irradiation of the crystal with light from the laser diode 44. (The diode 44 can be cooled by a pumped coolant or employ a heatsink). Both ends of the laser crystal 41 are preferably polished flat. The input face of the crystal 41 is preferably finished with a coating 52 for high transmittance at the pump wavelength and high reflectance of the output wavelength. The other end of the crystal 41 preferably includes an antireflective coating 50 for high transmittal of the output wavelength. The entire cavity of the reflector preferably is evacuated to provide thermal insulation and avoid moisture condensation.

For further details on the construction of cryogenic, solid-state lasers, see, for example, an article by Barnes et al., Vol. 190, *Society of the Photo-Optical Instrumentation Engineers*, pp. 297–304 (1979), NASA/JPL Technical Brief No. NPO-17282/6780 by Hemmati (June, 1988) and above-referenced U.S. Pat. No. 4,917,084, all of which are herein incorporated by reference.

Also shown in FIG. 10 is a tuning element 26 which can include, for example, a birefringent crystal 28 disposed along the beam path 58 at a slight offset from Brewster's angle. The crystal 28 can be tuned electro-optically by application of a voltage, as shown schematically in the figure. Alternatively, the laser wavelength can be tuned mechanically by tilting or rotating the crystal 28 relative to the beam path using techniques well known in the art.

Figure 12:
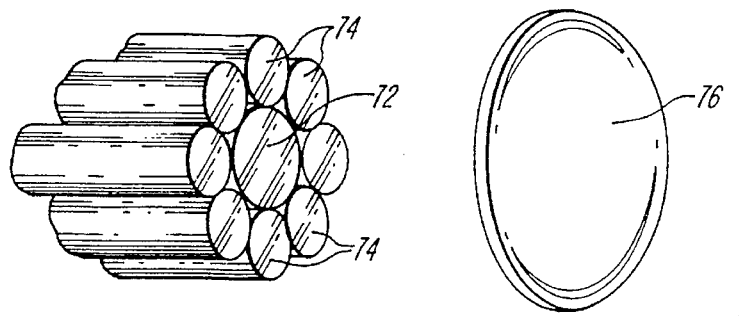
FIG. 12 is a front view of the laser delivery handpiece of FIG. 11.

In FIG., 11 a partial, cross-sectional side view of a handpiece 64 is shown, including a casing 70 adapted for gripping by the clinical user and multiple lumens disposed therein. With further reference to FIG. 12 as well, the handpiece serves to deliver laser irradiation suitable for biological tissue fusion via a central optical fiber 72 connected to laser source, as well as one or more additional illumination fibers 74 for the delivery of illumination light and the transmittal of reflected light. The surgical laser delivery fiber 72 is preferable a low, hydroxyl ion content silica fiber. As shown in FIG. 12, the handpiece 64 can deliver illumination light via fibers 74. In one embodiment, these fibers 74 can also be used to collect reflective light and deliver it to a controller. Alternatively, some of the fibers 74 can be devoted entirely to collection of reflected light. The handpiece 64 can further include one or more lens elements 76, as well as a transparent protective cover element or terminal lens 82.

Figure 13:
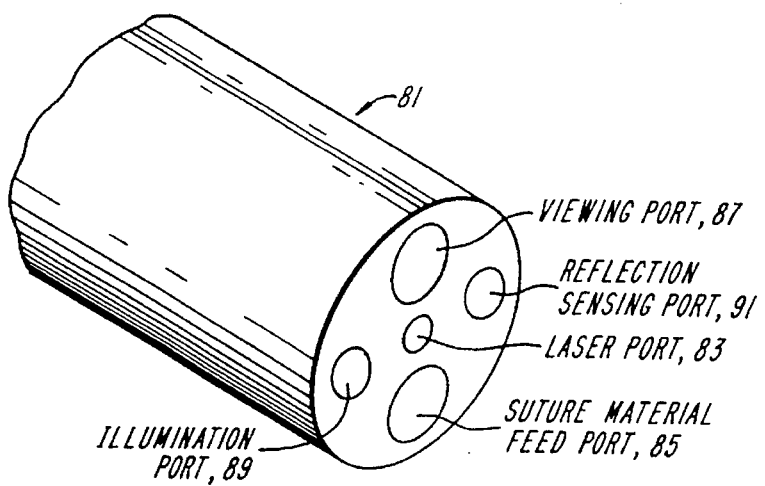
FIG. 13 front view of a surgical instrument incorporating both a suture means and a laser means according to the invention.

FIG. 13 shows an apparatus 81 for remote application of sutures according to the invention. The apparatus 81 can be incorporated into a catheter, endoscope or arthroscope and disposed adjacent to a remote anastomotic site. As shown, apparatus 81 includes a suture means 85 and a laser means 83. The suture port 85 delivers a photoreactive suture material to the anastomotic site, the suture material comprising a structure with at least a portion of the structure formed by a crosslinking agent such that upon irradiation of said suture means the crosslinking agent adheres to the biological material and thereby provides closure at said anastomotic site. The laser means 83 provides the necessary light energy in the form of laser radiation to effect crosslinking of the suture material at the anastomotic site. The apparatus 81 can also include a viewing port 87, an illumination port 89 and a reflectance sensing port 91 to provide a display and monitoring of the crosslinking process, as described in more detail below.

Figure 14:
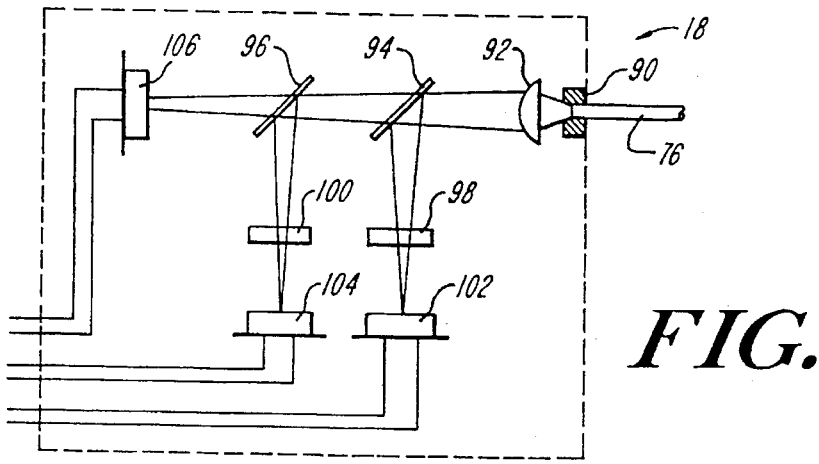
FIG. 14 is a more detailed schematic diagram of reflectance monitor for use in the present invention.

FIG. 14 is a more detailed schematic diagram of a reflectance monitor 18, including a coupling port 90 for coupling with one or more fibers 76 to receive reflectance signals from the handpiece of FIG. 4 or the apparatus of FIG. 13. The reflectance monitor 18 can further include a focusing lens 92 and first and second beam splitting elements 94 and 96, which serve to divide the reflected light into 3 (or more) different beams for processing.

As shown in FIG. 14, a first beam is transmitted to a first optical filter 98 to detector 102 (providing, for example, measurement of reflected light at wavelengths shorter than 0.7 micrometers). A second portion of the reflected light signal is transmitted by beam splitter 96 through a second optical filter 100 to detector 104 (e.g., providing measurement of light at wavelengths shorter than 1.1 micrometers). Finally, a third portion of the reflected light is transmitted to photodetector 106 (e.g., for measurement of reflected light at wavelengths greater than 1.6 micrometers). Each of the detector elements 102, 104, and 106 generate electrical signals in response to the intensity of light at particular wavelengths.

The detector elements 102, 104 and 106 preferably include synchronous demodulation circuitry and are used in conjunction with a modulated illumination source to suppress any artifacts caused by stray light or the ambient environment. (It should be apparent that other optical arrangements can be employed to obtain multiple wavelength analysis, including the use, for example, of dichroic elements, either as beamsplitters or in conjunction with such beamsplitters, to effectively pass particular wavelengths to specific detector elements. It should also be apparent that more than three discreet wavelengths can be measured, depending upon the particular application.) The signals from the detector elements can then be transmitted to a controller and/or a display element (as shown in FIG. 1).

In the controller, signals from the reflectance monitor are analyzed (as detailed below) to determine the degree of crosslinking which is occurring in the suture material and/or in the biological tissue exposed to the laser radiation. Such analysis can generate control signals which will progressively reduce the laser output energy over time as a particular site experiences cumulative exposure. The control signals can further provide for an automatic shut-off of the laser when the optimal state of crosslinking has been exceeded and/or the onset of carbonization is occurring.

Figure 15:
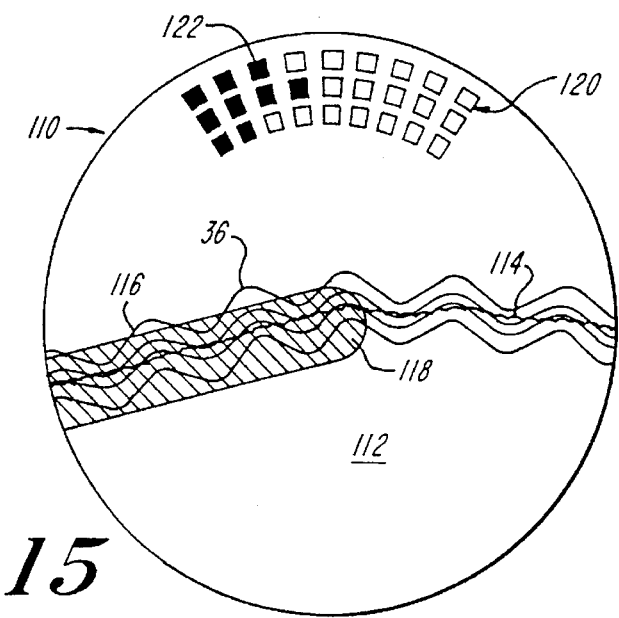
FIG. 15 is a schematic illustration of a clinical eyepiece view showing a "heads-up" display of reflectance measurements according to the invention.

As shown in FIG. 15, the data from the reflectance monitor can also be provided directly to the clinician. In FIG. 15, a simulated view from an eyepiece 110 is shown in which the field of view 112 includes a fissure or cleavage line 114 dividing separate bodies at an anastomotic site. Also shown within the field of view is the suture material 36, a fusion track 116 which has been formed by laser radiation, and a present exposure zone 118. Also displayed within the eyepiece 110 is a "heads-up" display of the reflectance values for the reflectance monitor of FIG. 14, including illuminated warning lights 122 which serve to indicate the reflectance intensity at particular wavelengths or other optical data indicative of the degree of crosslinking and/or tissue fusion.

In use, the apparatus of the present invention can be employed to analyze the degree of crosslinking by comparing the reflectance ratios of a site at two or more wavelengths. Preferably, intensity readings for three or more wavelength ranges are employed in order to accurately assess the degree of crosslinking and to ensure that the optimal state is not exceeded. The particular wavelengths to be monitored will, of course, vary with the particular tissue undergoing treatment. Although the tissue type, (e.g., blood-containing tissue or that which is relatively blood-free) will vary, the general principles of the invention, as disclosed herein, can be readily applied by those skilled in the art to diverse procedures in which the fusion of biological materials is desired.

For example, it is known that carbonization of many tissue types is accompanied by a decrease in visible light reflectance and an increase in infrared reflectance. Thus, the analyzing circuitry of the controller can be constructed to provide a warning (or automatically shut off the laser radiation) when darkening in the visible wavelengths occurs or when the ratio of visible to infrared values falls below a predefined level.

Moreover, when the material to be joined (e.g., aortic tissue) is relatively unpigmented, reliance on changes in the reflectance of visible light can be inaccurate, but infrared reflectance changes (e.g., above 1.1 micrometers) can reliably indicate the degree of crosslinking. (Lack of change in the visible reflectance is one of the reasons that tissues of this type are difficult to crosslink, as no change in the target's visible properties are observed until the tissue is overexposed to laser energy.) Consequently, the analyzing circuitry can monitor infrared reflectively changes (e.g., greater than about 1.0 micrometers) as an indicator of proper crosslinking.

Finally, the reflectance sensor can also be used as a proximity monitor to ensue that the laser is in fact disposed at a proper distance from the anastomic site. By measuring total reflectance (over the entire visible-infrared range or a portion thereof), a sudden drop in the reflectance value will typically be related to incorrect placement of the handpiece. Thus, the analyzing circuitry can sense the changes in reflectance and generate a warning to the user (or automatically shut off the system) until proper placement is achieved.

What is claimed:

1. A suture for joining biological material comprising a structure adapted for positioning at an anastomotic site, the structure further comprising at least one tensile strength-imparting element for resisting tensile and shearing forces and a photoreactive crosslinking agent coupled to the tensile strengthening element and positioned such that the crosslinking agent can contact said biological material at said site, such that upon irradiation of said structure the crosslinking agent adheres to the biological material to form a suture and the tensile strengthening element inhibiting tears in said structure.

2. The suture material of claim 1 wherein the structure is biodegradable over time in vivo.

3. The suture material of claim 1 wherein the crosslinking agent is responsive to laser radiation such upon irradiation the agent also bonds to the tensile strength-imparting element.

4. The suture material of claim 1 wherein the crosslinking agent comprises at least one agent chosen from the consisting of collagen, elastin, fibrin and albumin.

5. The suture material of claim 1 wherein the tensile strength-imparting element is a material selected from the group of pre-crosslinked segments of the same material that forms the photoreactive crosslinking agent, and strips and fibers of natural and synthetic biodegradable materials.

6. The suture material of claim 1 wherein the tensile strengthening element is connected to said cross-linking agent, such that, upon irradiation, the high strength element and biological material are joined to each other to enhance bond strength.

7. The suture material of claim 1 wherein the tensile strengthening element comprises a biodegradable fiber element.

8. The suture material of claim 1 wherein the tensile strengthening element comprises a polymeric fiber element.

9. The suture material of claim 1 wherein the tensile strengthening element further includes means for piercing said biological materials to enhance joinder.

10. The suture material of claim 1 wherein the structure is adapted to placed around a tubular biological structure for repair purposes.

11. The suture material of claim 10 wherein the structure is a tubular structure.

12. The suture material of claim 10 wherein the structure is a band structure adapted to be wrapped around a tubular biological structure.

13. The suture material of claim 10 wherein the structure further comprises at least one high tensile strength fiber element.

14. A suture material for joining biological material comprising a structure adapted for positioning at an anastomotic site, the structure further comprising:

at least one tensile strength-imparting element for resisting tensile and shearing forces a photoreactive crosslinking agent coupled to the element such that upon irradiation of said structure the crosslinking agent adheres to the biological material and the element inhibiting tears in said structure, and a detachable carrier means for situating the structure and crosslinking agent at the site such that the crosslinking agent can be placed in contact with said biological material prior to irradiation to facilitate joinder.

15. The suture material of claim 14 wherein the detachable carrier is substantially transparent to photo-irradiation and can be detached from said crosslinking agent following the bonding of the agent to the biological material.

16. A method for joining biological materials comprising:

applying a suture material at an anastomotic site, the suture material having a structure with at least one tensile strength-imparting element and at least a portion of said structure/brined by a photoreactive crosslinking agent;

delivering light energy to said site such that upon irradiation of said structure with said light energy the crosslinking agent adheres to the biological material and thereby provides closure at said anastomotic site and the tensile strength-imparting element serves to inhibit tears in the structure; and analyzing the degree of crosslinking within an exposure zone based on measurements of reflectance intensity at a plurality of wavelengths.

17. The method of claim 16 wherein the method further comprises measuring light reflected from said site; and controlling the laser in response to monitored changes in the reflectance of the light from the site to achieve crosslinking of the biological materials without thermal damage.

18. The method of claim 16 wherein the high tensile strength element is connected to said cross-linking agent, such that, upon irradiation, the high strength element and biological material are joined to each other to enhance bond strength to the anastomotic site prior to laser irradiation.

19. The method of claim 16 wherein the suture material further comprises a detachable carrier means which is substantially transparent to photo-irradiation, and the method further comprises irradiating the crosslinking agent and then detaching the career from the crosslinking agent following the bonding of the agent to the biological material.

20. The method of claim 16 wherein the suture material is a staple means for connecting the biological material and the method further comprises irradiating a portion of the staple means after it is applied.

21. The method of claim 16 wherein the method further comprises tuning the output wavelength of the beam of laser radiation to match the characteristic of the crosslinking agent or the biological materials.

* * * * *

UNITED STATES PATENT AND TRADEMARK OFFICE
CERTIFICATE OF CORRECTION

PATENT NO. : 5,569,239
DATED      : October 29, 1996
INVENTOR(S) : Edward L. Sinofsky It is certified that error appears in the above-indentified patent and that said Letters Patent is hereby corrected as shown below:

At column 10, line 63, please replace "said structure/brined by" with --said structure formed by--; and At column 12, line 6, please replace "the career from" with --the carrier from--

Signed and Sealed this

Eighteenth Day of August, 1998

Attest:

BRUCE LEHMAN

Attesting Officer    Commissioner of Patents and Trademarks